United States Patent [19]

Mauz et al.

[11] Patent Number: 5,079,156

[45] Date of Patent: Jan. 7, 1992

[54] CARRIER BONDED ENZYMES AND A PROCESS FOR THEIR PREPARATION

[75] Inventors: Otto Mauz, Liederbach; Siegfried Noetzel, Kelkheim; Bernhard Neumann, Siegen, all of Fed. Rep. of Germany

[73] Assignee: Hoechst Aktiengesellschaft, Frankfurt, Fed. Rep. of Germany

[21] Appl. No.: 238,855

[22] Filed: Aug. 31, 1988

Related U.S. Application Data

[60] Division of Ser. No. 131,335, Dec. 8, 1987, Pat. No. 4,906,715, which is a continuation of Ser. No. 898,749, Aug. 18, 1986, abandoned, which is a continuation of Ser. No. 680,461, Dec. 11, 1984, Pat. No. 4,695,788.

[30] Foreign Application Priority Data

Dec. 13, 1983 [DE] Fed. Rep. of Germany ....... 3344912

[51] Int. Cl.⁵ ............................................. C12N 11/06
[52] U.S. Cl. .................................... 435/181; 526/263
[58] Field of Search ............. 526/263, 258; 435/180, 435/181; 525/326.7; 530/389, 390

[56] References Cited

U.S. PATENT DOCUMENTS

| | | | |
|---|---|---|---|
| 3,619,371 | 11/1971 | Crook et al. | 530/389 |
| 3,964,973 | 6/1976 | Hradil et al. | 435/181 |
| 4,314,032 | 2/1982 | Murayama et al. | 521/52 |
| 4,568,706 | 2/1986 | Noetzel et al. | 526/304 |
| 4,767,620 | 8/1988 | Marz et al. | 526/302 |

FOREIGN PATENT DOCUMENTS 53-84043  7/1978  Japan ................... 435/181

*Primary Examiner*—Thurman K. Page
*Assistant Examiner*—Peter F. Kulkosky
*Attorney, Agent, or Firm*—Finnegan, Henderson, Farabow, Garrett and Dunner

[57] ABSTRACT

The invention relates to crosslinked polymers based on polyvinyl acylate or polyvinyl alcohol and having crosslinking agent units which are derived from crosslinking agents of the general formulae

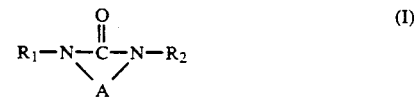

and/or

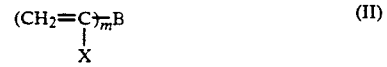

These products, inter alia, are particularly hydrolysis-resistant and can have high crosslinking densities.

The invention also relates to a process for preparing these polymers and to their use in chromatography and as carriers for biologically active substances.

20 Claims, No Drawings

CARRIER BONDED ENZYMES AND A PROCESS FOR THEIR PREPARATION

This is a division of application Ser. No. 07/131,335, filed Dec. 8, 1987, now U.S. Pat. No. 4,906,715, which was a continuation of application Ser. No. 06/898,749, filed Aug. 18, 1986, now abandoned, which was a continuation of application Ser. No. 06/680,461, filed Dec. 11, 1984 now U.S. Pat. No. 4,695,788.

The use of polymer gels for gel permeation chromatography of polymer solutions for the purpose of separating or purifying substances or for determining the molecular weight distribution has been known quite a long time. Polymer gels which are suitable for aqueous systems are referred to as hydrophilic, whereas those which can only be used in non-aqueous systems (organic solvents) are referred to as hydrophobic. Examples of hydrophobic gels are crosslinked polystyrenes, whereas hydrophilic gels are based on crosslinked dextrans, polyvinylpyrrolidone, polyacrylamide or polyvinyl alcohol. Any excessive tendency of these gels so swell and hence, for example, prevent high flow rates in gel permeation chromatography can be counteracted by increasing the degree of crosslinking.

There are already existing hydrophobic gels based on crosslinked polyvinyl acetate from which, by hydrolyzing the acetate groups, a hydrophilic gel based on crosslinked polyvinyl alcohol can be prepared. Here the important point, above all, is that the crosslinking must be highly resistant to hydrolysis.

A number of compounds have already been described as crosslinking agents for this purpose in the prior art For instance, German Patent 1,517,935 discloses for this purpose not only divinylalkylenes, divinyl and dialkyl esters of dicarboxylic acids and others but also divinyl or diallyl ethers of polyhydric alcohols, preference being given to butanediol divinyl ether (cf. in this context also Makromol. Chemie 176, pages 657 et seq. (1975)). The crosslinked polyvinyl acetates and polyvinyl alcohols which can be obtained according to said patent can also be in the form of macroporous beads. It is true that the crosslinking with butanediol divinyl ether is stable to hydrolysis, but this ether copolymerizes with vinyl acetate only relatively reluctantly, so that only relatively low crosslinking densities can be obtained with this crosslinking agent.

Other existing crosslinking agents such as ethylene glycol dimethyl acrylate or glycidyl methacrylate (U.S. Pat. No. 4,104,208) do not produce hydrolysis-resistant crosslinking and are not incorporated uniformly. Thus, the copolymerization parameters of vinyl acetate ($M_2$) and methyl methacrylate ($M_2$) are $r_1=0.01$ $r_2=20$. Similar copolymerization parameters are likely for the methacrylates mentioned here. So the two crosslinking agents mentioned are consumed at the start of the reaction; it is therefore impossible to obtain uniform incorporation.

It is also already part of the state of the art to use hydrophilic polymer gels for affinity chromatography for separating biologically active substances, i.e. for immobilizing such substances, and before this use to react the reactive groups of the polymer gel, which are usually OH groups, with so-called spacers. Spacers in this sense include inter alia epichlorohydrin (cf. German Offenlegungsschrift 2,102,514 and German Patent 2,421,789).

It is then the object of the present invention to provide a crosslinked polymer which is based on polyvinyl ester and in particular polyvinyl alcohol, which does not have the state of the art disadvantages, which, in particular is hydrolysis-resistant and is particularly suitable for use as an adsorbent in gel chromatography or as a carrier material for chemically covalently bonded biologically active substances, and which hardly impairs the activity of the chemically covalently bonded, biologically active substances and guarantees unimpeded flow of the substrates to be treated.

The invention accordingly relates to a crosslinked polymer which essentially comprises vinyl acylate units and units of a crosslinking agent which has the general formulae

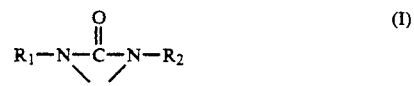

and/or

where $R_1$ and $R_2$ in the formula (I) can be identical or different and each denotes vinyl, 1-acyloxyvinyl, allyl or 2-acyloxyallyl, A represents a divalent hydrocarbon radical of 2 to 8 carbon atoms, B in the formula (II) stands for a divalent, trivalent or tetravalent hydrocarbon radical of 1 to 8 carbon atoms, m corresponds to the valency of this radical and X denotes acyloxy, the amount of these crosslinking agent units accounting for 0.1 to 60% by weight of the polymer.

Preferably, the acylate groups of the vinyl acylate units are partially or completely replaced by OH groups.

The invention also provides a process for preparing this crosslinked polymer by copolymerizing vinyl acylate with a crosslinking agent in the presence of a dispersion medium wherein the crosslinking agent has the above formulae (I) and/or (II). Preferably, the polymer thus obtained is subsequently partially or completely hydrolyzed.

Finally, the invention also concerns the use of the polymers according to the invention as adsorbents in chromatography or as carrier materials for biologically active substances.

The vinyl acylate units of the polymer according to the invention preferably contain 2 to 18 carbon atoms, in particular 2 to 6 carbon atoms, in the acylate radical. The latter is preferably an acetate or propionate radical. It is also possible for various acylate radicals to be present in the polymer, which is to say that the polymer can also be prepared with mixtures of appropriate vinyl acylates.

In the crosslinking agent of the formula (I), A preferably represents a branched or unbranched aliphatic hydrocarbon radical of 2 to 5 carbon atoms, in particular 2 or 3 carbon atoms. This hydrocarbon radical is particularly preferably an ethylene or propylene radical. If $R_1/R_2$ of this formula (I) stand for 1-acyloxyvinyl or 2-acyloxyallyl, the acyloxy group therein preferably contains 2 to 18 carbon atoms, in particular 2 to 6 carbon atoms. Acyloxy preferably denotes an acetate or propionate radical. The radicals $R_1/R_2$ preferably denote vinyl. A preferred crosslinking agent unit in the polymer according to the invention is correspondingly derived from N,N'-divinylethylene urea. This crosslinking agent brings about a particularly hydrolysis-resistant form of crosslinking. Another preferred representative is N,N',-divinylethylene urea.

The preparation of these compounds is known and is described, for example, in U.S. Pat. No. 2,541,152 and Ullmann, Encyklopadie der technischen Chemie [Encyclopedia of Industrial Chemistry], volume 23, 611 (4th edition).

In the crosslinking agent of the formula (II), B preferably denotes a divalent hydrocarbon radical, in particular a branched or unbranched alkylene radical of 2 to 6 carbon atoms, preferably 2 to 4 carbon atoms. In this instance the acyloxy group preferably has the same meaning as is described above for the R radical in the formula (I). An example of a preferred crosslinking agent of this type is 3,3-dimethylpentadiene 2,4-diacetate, which copolymerizes particularly readily with the vinyl acylate. Compounds of this type can be prepared, for example, by reacting the appropriate diketone, triketone or tetraketone with vinyl acylate or isopropenyl acylate in the presence of acid catalysts, the corresponding enol acylates being formed. The acetone which is formed at the same time has to be continuously removed out of the equilibrium mixture by distillation.

The amount of units of crosslinking agent (II) generally accounts for 0 to 100%, in particular 0 to 60%, of the total amount of crosslinking agent units in the polymer.

The total amount of crosslinking agent units in the polymer according to the invention is within the claimed ranges and depends on the crosslinking density desired for the specific intended use. For instance, in gel chromatography a high dimensional stability is desirable, which presupposes a high crosslinking density and hence a higher content of crosslinking monomer units. By comparison, a lower crosslinking agent density can be advantageous in other areas of use, for example as carrier material for enzyme reactions in a stirred vessel or for diagnostic agents. Crosslinking agent contents below 0.1% by weight, in most cases, no longer produce useful products. Crosslinking agent contents above 60% by weight are basically possible, but, as a rule, do not lead to further advantages.

Depending on the intended use, the amount of crosslinking agent units is preferably 1 to 50% by weight, in particular 1 to 40% by weight, of the polymer. For use as a carries material for biologically active substances, the lower limit is preferably 2.5% by weight, particularly preferably 10% by weight. If only crosslinking agent units of the formula (II) are present, their lower limit is particularly preferably 2.5% by weight.

For some uses, it can be of advantage for the polymer according to the invention also to contain monomer units of a monomer which is copolymerizable with vinyl acetate, their amount generally not exceeding 10% by weight of the total polymer and preferably being between 0.1 and 5% by weight. Examples of these monomers which may be used in the mixture are: N-vinylpyrrolidone, vinylene carbonate, (meth)acrylic acid, (meth)acrylnitrile, (meth)acrylamide, alkyl (meth)acrylates each of 2 to 12 carbon atoms, preferably 2 to 4 carbon atoms, in the alkyl radical, hydroxyalkyl esters of (meth)acrylic acid having 2 to 6 carbon atoms in the alkyl group, N-vinyl-N-alkyl-acetamide, styrene, α-methylstyrene and the like.

The crosslinked polymer according to the invention is preferably in the form of beads which are predominantly spherical in shape, whose average particle size in the dry, unswollen state is 20 to 800 μm, preferably 50 to 300 μm, and which preferably have a narrow particle size distribution. The most suitable particle size depends in each case in the main on the specific field of use. For instance, for a column method carried out in the absence of pressure an appropriately higher particle size would be chosen, within the abovementioned limits, than for a pressurized method. The beads of the polymer according to the invention are constituted predominantly macroporously. The average pore diameter is generally within the range from 2 to 10,000 nm, preferably 5 to 200 nm, in particular 20 to 200 nm.

The pore diameter (pore volume) can be determined by first of all determining the pore volume by the capillary pressure method (mercury porosimetry)(cf. in this context "Ullmanns Encyklopadie der technischen Chemie" [Ullmann's Encyclopedia of Industrial Chemistry], volume 5 (1980), pages 751-752). From the pore volume the average pore diameter can then be calculated by the equation given at the top of the left-hand column on page 752 of this reference. It is also possible to determine the pore size by scanning electron microscopy.

The acylate groups of the vinyl acylate units in the polymer according to the invention have preferably been hydrolyzed into OH groups, the degree of hydrolysis being generally more than 50%, preferably more than 70%. and in particular 90 to 100%. If the crosslinked polymer obtained from hydrolysis, namely polyvinyl alcohol, is to be used as a carrier material for biologically active substances, preferably at least a portion of the OH groups are occupied by so-called spacer groups, which are defined below. By contrast, for some purposes of gel chromatography it can be of advantage for at least some of the OH groups to be occupied by hydrophobing groups which no longer contain reactive radicals.

The polymers according to the invention are distinguished in particular by high resistance to hydrolysis combined with high crosslinking density. This high resistance to hydrolysis is of great importance not only in gel chromatography but also in the use as a carrier material for biologically active substances, such as enzymes. Carrier-supported enzymes are frequently employed for years in a strongly alkaline or strongly acid medium. This is especially true of "nonspecific hydrolases", which cleave ester or carboxamide bonds. As for the rest, the stable crosslinking is also advantageous in the hydrolysis of the acylate groups into OH groups in the polymers according to the invention.

The polymers according to the invention are suitable, inter alia, for use as the stationary phase in gel chromatography and as a carrier material for biologically active substances.

The crosslinked polymers according to the invention are prepared in conventional manner, preferably under bead polymerization conditions in the presence of a dispersion medium and of a dispersion stabilizer and in the absence or presence of further additives and in the absence or presence of a free-radical initiator and preferably of an inert diluent and with the exclusion of oxygen.

Suitable dispersion media for carrying out the bead polymerization are in the main compounds which are liquid under normal conditions and have a boiling point of above 60° C., preferably within the range from 85° to 300° C., and in which, under the polymerization conditions, the monomers, the polymer and preferably also the initiator are insoluble or at any rate only sparingly soluble, in order to suppress any emulsion polymerization. The ratio of the monomer phase to the dispersion medium phase can vary within wide limits, for example between 0.5:1 and 1:50, preferably 1:1 and 1:15 (by weight). According to the invention the preferred dispersion medium is water. The water advantageously contains a buffer which operates within the alkaline range and makes the hydrogen ion concentration resistant to the acid formed by hydrolysis of vinyl acylate. This buffer preferably H consists of $Na_2HPO_4/NaH_2PO_4$ or $NaHCO_3$.

The dispersion stabilizer, which is to prevent the beads from agglomerating in the course of the polymerization, can be one of the compounds known for this purpose. It is preferably a hydrophilic polymer, such as polyvinylpyrrolidone, polyvinyl alcohol, polyacrylamide, polyethylene glycol, methylcellulose or ethylene oxide/propylene oxide copolymer. Polyvinylpyrrolidone is particularly preferred for this purpose. These dispersion stabilizers are effective in amounts as low as 0.001% by weight of the total amount of monomer. Usually the amounts used range from 0.005 to 50% by weight, preferably 0.01-20% by weight (based on the total amount of monomer).

The addition of an electrolyte to the aqueous phase (if the dispersion medium is water), for example of a salt such as sodium chloride, is generally advantageous, since this has the effect of almost completely displacing the monomer out of the outer phase and hence of almost completely stopping emulsions from forming and, additionally, of increasing the yield of beads. The added electrolyte, moreover, can also, to some extent, have the action of a protective colloid. This electrolyte is usually used in amounts of up to 50% by weight, preferably up to 30% by weight, based on the dispersion medium.

According to the invention, suitable free-radical initiators should be readily soluble in the monomer phase and be as sparingly soluble as possible in the liquid dispersion medium. Examples thereof are organic peroxides, such as di-tert-butyl peroxide, dibenzoyl peroxide, cumene hydroperoxide or cyclohexanone peroxide, and aliphatic azo compounds, such as $\alpha,'$-azodiisobutyronitrile, azobiscyanovaleric acid, 1,1'-azocyclohexane-1,1'-dicarbodinitrile or azodicarboxamide. Appropriate redox systems can also be used. The amount of initiator is usually 0.01-5% by weight, preferably 0.1 to 2% by weight (based on the total amount of monomer). It is also possible to initiate the polymerization by radiation in the absence or presence of an initiator.

To obtain as high a porosity as possible in the bead polymers, certain inert, liquid components (diluents) are added to the polymerization system or preferably the monomers. For the purposes of the present invention, these diluents are substances in which the monomers are readily soluble or with which the monomers are miscible, but which, on the other hand, are virtually insoluble in the dispersion medium and hence are immiscible therewith. Diluents of this type and their mode of action are described, for example, in German Patent 1,517,935 and Makromol. Chemie 176, pages 657 et seq. (1975).

The most suitable diluent or diluent mixre is readily determined by a few simple routine experiments. The pore size can be affected by the nature, composition and amount of the inert component, but it also depends on the amount of crosslinking component.

The diluents can be used either alone or mixed and be solvents or coagulants for polyvinyl acetate. Examples are: alkanols, such as butanol, cyclohexanol, isooctanol or glycol, esters, such as butyl acetate, butylglycol acetate or glycerol triacetate, amides, such as dimethylformamide, dimethylacetamide or pyrrolidone, ketones, such as acetone or cyclohexanone, ethers, dialkyl ethers of at least 6 carbon atoms, such as di-n-butyl ether, di-n-amyl ether or diphenyl ether, and hydrocarbons, such as hexane, benzene, isooctane or paraffin oil. The preferred diluents, for water as the dispersion medium, are dialkyl ether of at least 6 carbon atoms, such as di-n-butyl ether or di-n-amyl ether. Other preferred diluents are polyglycols which are formed by addition of a mixture of ethylene oxide and propylene oxide or of propylene oxide alone onto an alcohol, for example butanol as the starting molecule, and which may have a random distribution of ethylene oxide and propylene oxide or be block polymers of ethylene oxide and propylene oxide where poly(oxyethylene) units are added to both ends of the poly(oxypropylene) chain.

The amount of added diluent is largely variable. It depends, inter alia, on the monomer composition, in particular the crosslinking agent content, on the desired porosity (pore size), and on the exact purpose intended for the polymer. Thus, in the case of a high degree of crosslinking it is advisable for the amount of diluent to be high as well in order to obtain a certain porosity (pore size). Similarly, for a given degree of crosslinking the porosity (pore size) will be higher the higher the amount of diluent. Naturally, there are limits to the amount of diluent, since otherwise the mechanical strength becomes insufficiently low. In most cases, satisfactory results are obtained if the volume of diluent is 0.02 to 5 times, preferably 0.04 to 3 times, the volume of monomer used.

The vinyl acylate, the crosslinking agent and the further comonomer(s) are used in such amounts as to produce a polymer containing the abovementioned levels of monomer units.

The process according to the invention is advantageously carried out at temperatures of usually 20°-150° C., preferably 20°-100° C., and under a pressure of 1-10 bar, preferably 1-5 bar, in a reaction vessel equipped with a stirrer. The particle size of the bead polymer is set in conventional manner by the stirrer speed and the phase ratio The reaction vessel is preferably vacuum-tight and can be equipped with reflux condenser, addition funnel, gas inlet tube and temperature-measuring means. The vessel is generally heated and cooled by means of a liquid bath, for example an oil bath or water bath. It is advantageous to carry out the process according to the invention in the absence of atmospheric oxygen. For this reason the reaction vessel is flushed before the start with an inert gas, preferably nitrogen.

After the polymerization reaction has ended, the unreacted monomers are removed out of the reaction vessel, for example by vaporization under reduced pressure, preferably under a pressure of 0.1-15 mm Hg. After the residual monomers have been removed, the dispersion medium is separated from the solid polymer, for example by decanting, filtering or sucking off the supernatant liquor. The diluent, if used, can be removed beforehand by steam distillation. Afterwards the polymer is washed, if necessary, with low-boiling organic solvents, for example a hydrocarbon, a lower alcohol or acetone, and is finally dried at a temperature of usually 20°–100° C., preferably 20°–80° C., ideally under reduced pressure.

The polyvinyl acetate gel thus obtained is not hydrophilic; the ester group has to be hydrolyzed before use in water. The hydrolysis can be carried out in conventional manner under alkaline conditions by swelling the product in an alcohol, such as, for example, methanol, and adding aqueous alkali, such as, for example, sodium hydroxide solution, or by transesterifying the alcohol-swollen product with catalytic amounts of acid or base while the ester formed is continuously removed by, for example, distillation (cf. German Patent 1,517,935). The hydrolysis can be discontinued at any stage, so that the degree of hydrophilicity of the gel can be set in accordance with the intended use.

If the crosslinked polyvinyl alcohol gel in bead form is used as a carrier for biologically active substances which are to be fixed onto the carrier by covalent bonding, it is in many cases advantageous to modify the gel beforehand with so-called spacers. For the purposes of the present invention, spacers are compounds which react both with the support polymer and the biologically active substance and form a bridge, as it were, between the two. The reaction of the bead polymer with the spacer can take place either directly or preferably after prior hydrolysis of the acylate groups. The degree of conversion depends, inter alia, on the bulkiness of the spacer and the accessibility of the acylate group or of the secondary hydroxyl groups formed therefrom According to the invention, suitable spacers are the homo- and hetero-bifunctional compounds which are known for this purpose and whose second functional group takes on the coupling to the biologically active substance to be fixed (cf. German Patents 2,421,789 and 2,552,510, Ullmanns Encyclopadie der technischen Chemie [Ullmann's Encyclopedia of Industrial Chemistry], 4th Edition, Volume 10, page 540 and "Characterization of Immobilized Biocatalysts", Verlag Chemie, Weinheim, 1979, page 53).

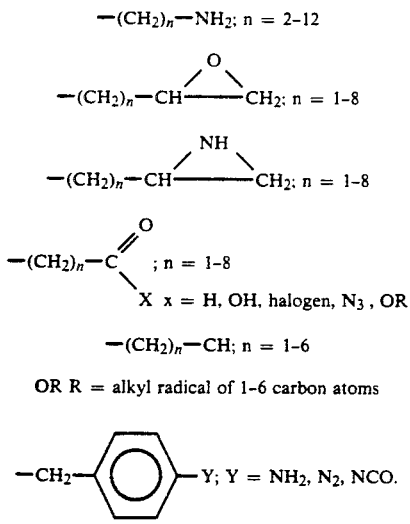

According to the invention, preferred spacers bring about hydrolysis-resistant chemical bonds and include epichlorohydrin or its homologs ($\alpha,\zeta$, -epoxy-$\omega$-halogenoalkanes). The reaction of the polyvinyl alcohols (polyvinyl acylates) takes place in the absence or presence of a solvent, preferably in the presence of a catalyst. The reaction generally takes between 30 minutes and 24 hours, depending on the temperature, which can be between room temperature and the refLux temperature of epichlorohydrin (113°–115° C.). Examples of suitable catalysts are NaOH (in powder form), aqueous alkalis, dimethylformamide, triethylamine and other acid acceptors.

For the purposes of the present invention, biologically active substances are known natural or artificial substances of in vivo or in vitro activity, such as enzymes, activators, inhibitors, antigens, antibodies, vitamins, hormones, effectors, antibiotics, proteins and the like. Proteins also include proteins having certain non-protein substituents, such as metal ions, polysaccharides, porphyrin groups, adenine dinucleotide, ribonucleic acid, phospholipids and so on. Biologically active substances even include polypeptide fragments, for example the active parts of enzyme molecules.

According to the invention, enzymes are preferred among the abovementioned biologically active substances Examples of enzymes are urease, penicillin acylase, D-aminoacid oxidase, adenyl deaminase, alcohol dehydrogenase, asparaginase, carboxypeptidase, chymotrypsin, diphosphoesterase, $\alpha$-glucosidase, glucose isomerase, glucose oxidase, glucose-6-phosphate dehydrogenase, hexokinase, invertase, $\zeta$-lactamase, Lactase, Lactate dehydrogenase, various Lectins, AND kinase, neuraminidase, apin, perosidase, alkaline and acid phosphatases, 5=-phosphodiesterase, pyruvate kinase, ribonuclease and trypsin.

Examples of other biologically active substances are hormones, such as insulin and various pituitary hormones, proteins of the gamma-globulin fraction, for example antibodies of classes G, M, A, D and E, other blood factors, for example antihemophilic factor, the blood-clotting factors, specific antibodies, for example hepatitis, poliomyelitis, measles, mumps, influenza or rabbit antibodies, antigens, such as hepatitis, polyomyelitis, measles, mumps, influenza or rabbit antigens for purifying or stimulating suitable antibody reactions in which the antigen (once insolubilized) remains in the insoluble form and consequently cannot penetrate and damage the body, as well as general body proteins, such as hemoglobin or albumin.

The anchoring reaction with the biologically active substance is carried out in conventional manner, as described for example in German Offenlegungsschrift 2,407,340 or German Patents 2,215,687, 2,421,789 and 2,552,510. The reaction usually takes place at room temperature, i.e. at +40° C. or below, the latter in particular when the biologically active substance to be anchored is unstable by nature; in this case the temperatures are then below +10° C., preferably at 0° to +5° C.

The anchoring reaction preferably takes place at around a neutral pH, for example pH 5-9, since in this pH range most of the biologically active substances are at their most stable. Nor, as a rule, is it necessary to maintain more strongly acid or alkaline conditions, since the macroporous bead polymers undergo rapid reaction with most of the substances in question even in the neutral range. The resulting bond affords sufficient stability for long storage periods and high stability in operations The invention is illustrated in more detail by the following Examples.

EXAMPLE 1

An organic phase comprising a solution of 97.5 g of vinyl acetate, 2.5 g of divinylethyleneurea and 0.1 g of azoisobutyronitrile was suspended with stirring in an aqueous phase comprising 4.2 g of $Na_2HPO_4$, pb 0.25 g of $NaH_2PO_4$, 7.0 g of polyvinylpyrrolidone and 700 ml of $H_2O$ under nitrogen in a flask equipped with a stirrer, a thermometer and a reflux condenser. The polymerization was started by heating to 75° C. by means of a hot bath. After two hours the temperature was raised to 85° C. A further two hours later the polymerization was complete. The suspension obtained was cooled down by pouring into ice, the finely dispersed emulsion was repeatedly decanted off, and the polymer was filtered off and dried. The amount of dry product obtained was 80 g.

To hydrolyze the product, 50 g thereof were swollen in methanol, and a solution of 50 g of NaOH in $H_2O$ was added at 25° C. without heating or countercooling. After twelve hours the product was filtered off, was washed with plenty of water until neutral, and was dried.

The products were used in gel chromatography. The unhydrolyzed gel was found to have an exclusion molecular weight of 1,200 for polystyrene in tetrahydrofuran. The hydrolyzed product had an exclusion molecular weight of 1,100 for polyethylene glycol in water.

EXAMPLE 2

The polymerization of Example 1 was carried out in the presence of 140 g of NaCl in the aqueous phase When the reaction was ended by pouring the suspension into ice-water, all the bead polymer immediately settled out, so that almost no emulsified content was obtained. The isolatable yield of bead polymer was above 90% (based on the polymerizable phase).

The exclusion molecular weight of the gel for polystyrene in tetrahydrofuran, rose to 1,500; after the hydrolysis the exclusion molecular weight was found to be 1,300 for polyethylene glycol in water.

EXAMPLE 3

The polymerization of Example 1 was repeated, except that the crosslinking component comprised 2.0 g of divinylethyleneurea and 0.5 g of 3,3-dimethylpentadiene 2,4-diacetate.

The gel chromatography data corresponded to those of Example 1.

The 3,3-dimethylpentadiene 2,4-diacetate was prepared as described below by acylating 3-methylbutan-2-one with acetic anhydride in the presence of a Lewis acid and subsequently reacting the resulting diketone with isopropenyl acetate:

330 g (3.84 mol) of freshly distilled 3-methylenebutanone were mixed with 500 g (5 mol) of technical acetic anhydride (95%) in a flask, and 160 g (1.15 mol) of $ZnCl_2$ were added with stirring under a stream of nitrogen. The contents of the flask were heated at 120° C. for 3 hours, were cooled down, and were distilled in a water jet vacuum.

This produced 363 g of a crude product having a boiling point of 62° C. (12 mm Hg) and a GC purity of Renewed distillation of this substance in a water jet vacuum produced 289 g of a uniform product having a boiling point of 60° C. (12 mm Hg) which, on 1H-NMR analysis, proved to be 3,3-dimethylpentane-2,4-dione (singuletts at 1.3 ppm and 2.05 ppm).

110 g of 3,3-dimethylpentane-2,4-dione were mixed with 500 g of dry isopropenyl acetate under nitrogen, and g of p-toluene sulfonic acid were added. The mixture was heated to the reflux temperature under a short packed column, and for several days distillate fractions were taken off at between 54° C. and 90° C. for brief periods at 12-hour intervals over several days. The composition of the reaction mixture was monitored by gas chromatography. After the reaction period of 6 days was over, the acid catalyst was neutralized by adding carbonate, and the reaction mixture was quickly distilled off in a water jet vacuum. Renewed distillation under atmospheric pressure served to remove unreacted isopropenyl acetate. Renewed distillation under a water jet vacuum produced 39 g (87.5° C./12 mm Hg) of a 100% pure substance by gas chromatography. This product was 3,3-dimethylpent-1-en-4-on-2-yl acetate (1H-NMR Singqlett at 1.3 ppm and 2.1 ppm, .Duplett at 4.9 ppm).

On further distillation the remainder of the crude product produces under an oil pump vacuum of 0.01 mm Hg a product mixture of a monoenol acetate and a second, higher-boiling compound. This produced, between 54° C. and 65° C. under 0.01 mm Hg, an additional 15 g of a dienol acetate in a purity of 93% (GC).

EXAMPLE 4

To carry out a heterogeneously crosslinking bead polymerization, a solution of 80 g of vinyl acetate, 20 g divinylethyleneurea, 1 g of azoisobutyronitrile and 200 g of n-heptanol was dispersed and polymerized in a solution of 0.175 g of $NaH_2PO_4$, 3 g of $Na_2HPO_4$ and 5 g of polyvinylpyrrolidone in 500 ml of water. The temperature variation corresponded to that of Example 1. After four hours the diluent was removed by steam distillation, and the product was isolated. The yield was 77.7 g of completely spherical clear bead polymer. The average particle diameter was about 30 μm (stirrer speed 460 rpm.)

The product had a bulk volume of 1.55 ml/g. In tetrahydrofuran its gel bed volume was 5.77 ml/g and the exclusion molecular weight for polystyrene was 80,000. The hydrolyzed product had a bulk volume of 1.54 ml/g, which rose on swelling in water to 5 ml/g, and had an exclusion molecular weight for polyethylene glycol of 20,000.

20 g of the hydrolyzed bead copolymer were allowed to swell at room temperature in 200 ml of epichlorohydrin for 24 hours. The temperature was then raised with slow stirring to 113°-115° and maintained for 4 hours. After cooling down the mixture was filtered with suction, and the copolymer was repeatedly triturated for 1-hour periods at a time in acetone The acetone-moist copolymer was dried at 50° C. in a vacuum cabinet to a constant weight. The epoxy equivalent weight was 244 (as measured by Axen method: Acta Chem. Scan-d Volume 29 (1975) No. 4).

EXAMPLE 5

The polymerization of Example 4 was repeated, except that the diluent was replaced by a mixture of 80 g of 2-ethylhexanol and 20 g of a polyglycol of ethylene oxide and propylene oxide (weight ratio 1:1; random distribution) having a molecular weight of about 1,200 and obtained by adding ethylene oxide and propylene oxide onto butanol as the starter. ("Polyglykol B 11/50" from HOECHST AG).

On isolation this produced 76 g of a chalk-white spherical bead polymer whose particle size was 50 to 200 μm at a stirrer speed of 460 rpm.

EXAMPLE 6

The polymerization of Example 4 was repeated, except that the diluent was replaced by a mixture of 70 g of 2-ethylhexanol and 30 g of a polyglycol having a molecular weight of about 700 and obtained by adding propylene oxide onto butanol as the starter ("Polyglykol B 01/20" from HOECHST AG).

On isolation this produced 82 g of a chalk-white spherical bead polymer whose particle size was 50 to 200 μm at a stirrer speed of 460 rpm.

EXAMPLE 7

The polymerization was repeated, except that the diluent was replaced by a mixture of 80 g of 2-ethylhexanol and 20 g of a polyglycol of ethylene oxide and propylene oxide (weight ratio: 4:1; random distribution; molecular weight: about 5,000) obtained by adding ethylene oxide and propylene oxide onto butanol as the starter ("Polyglykol P 41/300" from HOECHST AG).

On isolation this produced 68 g of a chalk-white spherical bead polymer whose particle size was within the range from 50 to 200 μm at a stirrer speed of 460 rpm.

EXAMPLE 8

The polymerization of Example 4 was repeated, except that the diluent was replaced by a mixture of 80 g of 2-ethylhexanol and 20 g of a polyether glycol of polyoxypropylene and polyoxyethylene having 10% by weight of polyoxyethylene in the total molecule, the polyoxyethylene units having been added to both ends of the polyoxypropylene chain (molecular weight: about 1,750)("Pluronic polyol 61" from BASF, Wyandotte Corp ).

On isolation this produced 72 g of a chalk-white spherical bead polymer whose particle size was in the range from 50 to 200 μm at a stirrer speed of 460 rpm.

EXAMPLE 9

The polymerization of Example 4 was repeated, except that the diluent was replaced by a mixture of 100 g of 2-ethylhexanol and 100 g of di-n-butyl ether. On isolation this produced 83 g of a chalk-white completely spherical bead polymer whose particle size was 70 μm at a stirrer speed as in Example 4.

The bulk volume of the product was 2.81 ml/g, and in tetrahydrofuran this had a gel bed volume of 7.48 ml/g and an exclusion molecular weight for polystyrene of $2 \times 10^6$. The hydrolyzed product had a bulk volume of 1.6 ml/g, the gel bed volume in water was 12.8 ml/g, and the exclusion molecular weight for polyethylene glycol was $2 \times 10^6$.

EXAMPLE 10

The polymerization of Example 4 was repeated, except that the dispersed phase comprised 70 g of vinyl acetate, 30 g of divinylethyleneurea, 1 g of azodiisobutyronitrile and 158 g of di-n-butyl ether. This produced 77 g of a white bead polymer having an average diameter of 200 μm.

The bulk volume was 2.9 ml/g, and the gel bed volume in tetrahydrofuran was 7.45 ml/g. The exclusion molecular weight of the product could not be determined by gel chromatography: polystyrene having a molecular weight of 25,000,000 was eluted with almost the internal volume. Scanning electron micrographs showed pores of more than 100,000 Å in diameter.

The hydrolyzed product had a bulk volume of 6.5 ml/g, which showed that the skeleton structure had been completely preserved. The gel bed volume in water was 14.5 ml/g; in the analysis by gel chromatography, polyethylene glycol having a molecular-weight of $3.8 \times 10^6$ had access to almost the entire internal volume.

10 g of the hydrolyzed copolymer were allowed to swell in 100 g of epichlorohydrin for 24 hours, and the temperature was then gradually raised with stirring to 110° and maintained for 12 hours. After cooling down to room temperature the mixture was filtered off with suction, and the copolymer was repeatedly stirred out slowly in acetone for 2 hours at a time. The drying took place at 50° C. in a vacuum cabinet. The epoxy equivalent weight was 105 umol per g of carrier substance.

Reaction of the bead-shaped polymer carrier according to the invention with biologically active substances

EXAMPLE 11

800 μl of a trypsin solution (6.25 mg/ml, 345 U/ml) were added to 100 mg of a carrier prepared as in Example 4. 1M potassium phosphate buffer was added to bring the enzyme solution to pH 7.8, and $1.6 \times 10^{-2}$ M benzamidine solution was added to stabilize the active center of the enzyme. The duration of fixing of the enzyme to the carrier was 72 hours at 25° C. The trypsin of bonded covalently to the carrier was then filtered off with suction via a glass fritte, and the residue was washed repeatedly with 1 M sodium chloride solution and then with buffer solution. The yield of moist material on the filter was 324 mg. The measurement was carried out at 37° and pH 7.8 with an autotitrator using N'-benzoyl-L-arginine ethyl ester hydrochloride (BAEE) and produced a value of 227.5 U/g in the moist state or 356 U/g based on the dry weight. From the starting and wash water activities the fixation yield could be calculated as 20%.

EXAMPLE 12

1500 μl of a urease solution (30 mg/ml, 51 U/ml) brought to pH 8.0 with 1 M potassium phosphate buffer were added to 200 mg of an epoxidized carrier prepared as in Example 10. After a period of fixation of 16 hours at room temperature the carrier was repeatedly washed with 1M sodium chloride solution and then with buffer solution. The yield of moist carrier on the filter was 754 mg. The measurement with an autotitrator at 30° and pH 8.0 using urea as substrate revealed an activity of 100 U/g (moist) or 377 U/g based on the dry weight of the carrier. From the starting and wash water activities it was possible to calculate a fixation yield of 98%.

We claim:

1. A carrier-bonded biologically active substance wherein said carrier is a crosslinked polymer which consists essentially of (a) vinyl acylate units and (b) units of at least one crosslinking agent of the formula

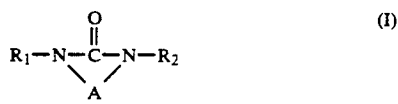

in the presence or absence of (c) units derived from an additional monomer which is copolymerizable with (a) wherein $R_1$ and $R_2$ in the formula (I) are identical or different and each denotes vinyl-, 1-acyloxyvinyl, allyl-, or 2-acyloxyallyl, A represents a divalent hydrocarbon radical of 2 to 8 carbon atoms, the units of crosslinking agent accounting for 0.1 to 60% by weight of the polymer and wherein the acylate groups of the vinyl acylate units are at least partially hydrolyzed and wherein said biologically active substance is bonded to said carrier through a spacer which contains the group

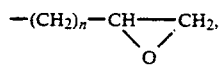

in which n denotes and integer of 1 to 8.

2. The carrier-bonded biologically active substance as claimed in claim 1 wherein the spacer is epichlorohydrin and said polymer contains vinyl acetate units.

3. The carrier-bonded biologically active substance as claimed in claim 1, wherein the biologically active substance is a natural or artificial substance of in vivo or in vitro activity.

4. The carrier-bonded biologically active substance as claimed in claim 1, wherein the biologically active substance is n enzyme selected from urease, trypsin, penicillin, acylase, chymotrypsin and carboxypeptidase.

5. The carrier-bonded substance as claimed in claim 1, wherein the acyloxy group in the radicals $R_1$ and $R_2$ of the formula (10 or the acyloxy radical in the formula (II) has 2 to 6 carbon atoms and B in formula (II) denotes a divalent hydrocarbon radical.

6. The carrier-bonded substance as claimed in claim 1, wherein the units of crosslinking agent account for 1 to 50% by weight of said polymer.

7. The carrier-bonded substance as claimed in claim 1, wherein at least 10% by weight of the acyloxy groups of the vinyl acylate units are replaced by hydroxyl groups.

8. The carrier-bonded substance as claimed in claim 1, wherein the polymer is in the form of macroporous beads with an average particle size of from 20 to 800 μm and an average pore diameter of from 2 to 10,000 nm.

9. A process for preparing a carrier-bonded biologically active substance comprising preparing a crosslinked polymer consisting essentially of vinyl acylate units and units of at least one crosslinking agent of the formula

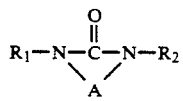

wherein $R_1$ and $R_2$ in the formula (I) are identical or different and each denotes vinyl-, 1-acyloxyvinyl, allyl-, or 2-acyloxy-allyl, A represents a divalent hydrocarbon radical of 2 to 8 carbon atoms the units of crosslinking agent accounting for 0.1 to 60% by weight of the polymer comprising the steps of: bead polymerizing (i) vinyl acylate with (ii) the crosslinking agents of formula (I) in the presence or absence of (iii) an additional monomer which is present in an amount not exceeding 10% by weight of the total polymer, and which is copolymerizable with the vinyl acylate, said bead polymerizing step occurring at a temperature of 20° C. to 150° C. and under a pressure of 1 to 10 bar in the presence of (iv) a dispersion medium; (v) at least one inert diluent present in a volume of 0.02 to 5 times the volume of monomers used, (vi) a dispersion stabilizer and in the absence or presence of, (vii) a further additive and (viii) a free-radical initiator with the exclusion of oxygen, and hydrolyzing at least partially the acylate groups of the resulting polymer to obtain an at least partially hydrolyzed product, treating said product by modification with a spacer to introduce the group

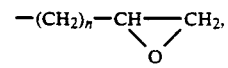

in which n denotes an integer of 1 to 8 followed by treating with a biologically active substance.

10. The process as claimed in claim 9, wherein the vinyl acylate is vinyl acetate and the spacer is eipchlorohydrin.

11. The process as claimed in claim 9, wherein the dispersion medium is an alkaline aqueous buffer solution and contains 0-50% by weight of an electrolyte.

12. The process as claimed in claim 9, wherein the dispersion medium contains a nonionic surfactant as the dispersion stabilizer.

13. The process as claimed in claim 9, wherein the polymerization step is carried out in the presence of a dialkyl ether of at least 6 carbon atoms as the inert diluent.

14. The process as claimed in claim 9, wherein the acyloxy group in the radical $Sr_1$ and $R_2$ of the formula (I) or the acyloxy radical in the formula (II) has 2 to 6 carbon atoms and B in formula (II) denotes a divalent hydrocarbon radical.

15. The process as claimed in claim 9, wherein the units of crosslinking agent account for 1 to 50% by weight of said polymer.

16. The process as claimed in claim 9, wherein at least 10% by weight of the acyloxy groups of the vinyl acylate units are replaced by hydroxyl groups.

17. The process as claimed in claim 9, wherein the hydrolysis is carried out by swelling the resulting polymer in an alcohol, and adding an aqueous alkali or by swelling said resulting polymer in an alcohol and transesterifying said polymer with catalytic amounts of acid or base.

18. The process as claimed in claim 9, wherein the reaction with the spacer takes place at +40° C. or below at a pH of 5-9.

19. A process as claimed in claim 9, wherein the resulting polymer is in the form of macroporous beads with an average particle size of 20 to 800 μm and an average pore diameter from 2 to 10,000 nm.

20. The process as claimed in clam 9, wherein the biologically active substance is an enzyme selected from urease, trypsin, penicillin, acylase, chymotrypsin and carboxypeptidase.

* * * * *